(12) United States Patent
Hojo et al.

(10) Patent No.: US 8,476,472 B2
(45) Date of Patent: Jul. 2, 2013

(54) (3R)-L-MENTHYL 3-HYDROXYBUTYRATE, PROCESS FOR PRODUCING THE SAME, AND SENSATE COMPOSITION COMPRISING THE SAME

(75) Inventors: Kazuma Hojo, Hiratsuka (JP); Takashi Aida, Tokyo (JP); Kenya Ishida, Hiratsuka (JP)

(73) Assignee: Takasago International Corporation, Tokyo (JP)

( * ) Notice: Subject to any disclaimer, the term of this patent is extended or adjusted under 35 U.S.C. 154(b) by 386 days.

(21) Appl. No.: 12/766,162

(22) Filed: Apr. 23, 2010

(65) Prior Publication Data

US 2010/0280110 A1 Nov. 4, 2010

Related U.S. Application Data

(60) Provisional application No. 61/232,550, filed on Aug. 10, 2009.

(30) Foreign Application Priority Data

Apr. 24, 2009 (JP) ................................. 2009-106605

(51) Int. Cl.
C07C 69/66 (2006.01)

(52) U.S. Cl.
USPC ........................................................ 560/188

(58) Field of Classification Search
None
See application file for complete search history.

(56) References Cited

U.S. PATENT DOCUMENTS

| 4,459,425 A | 7/1984 | Amano et al. |
| 2002/0035283 A1 | 3/2002 | Saito et al. |
| 2002/0198412 A1 | 12/2002 | Green et al. |
| 2007/0078279 A1 | 4/2007 | Mettler |
| 2007/0178123 A1 | 8/2007 | Levenson et al. |
| 2008/0175800 A1 | 7/2008 | Schoening et al. |
| 2009/0275669 A1 | 11/2009 | Aida et al. |

FOREIGN PATENT DOCUMENTS

| JP | 47-16647 A | 9/1972 |
| JP | 47-16648 A | 9/1972 |
| JP | 48-33069 A | 5/1973 |
| JP | 58-88334 A | 5/1983 |
| JP | 61-194049 A | 8/1986 |
| JP | 2-290827 A | 11/1990 |
| JP | 5-255186 A | 10/1993 |
| JP | 5-255217 A | 10/1993 |
| JP | 6-65023 A | 3/1994 |
| JP | 7-82200 A | 3/1995 |
| JP | 7-118119 A | 5/1995 |
| JP | 11-302226 A | 11/1999 |
| JP | 2001-294546 A | 10/2001 |
| JP | 2002-037760 A | 2/2002 |
| JP | 2007-002005 A | 1/2007 |
| JP | 2007-509874 A | 4/2007 |

OTHER PUBLICATIONS

Cainelli et al., Journal of the Chemical Society, Perkin Transactions 1: Organic and Bio-Organic Chemistry (1972-1999) (1987), (12), 2637-42.*
Database Caplus Chemical Abstracts Service, Columbus, Ohio, US; Database Accession No. 1988:528647, Abstract of Cainelli et al., Journal of the Chemical Society, Perkin Transactions 1: Organic and Bio-Organic Chemistry (1972-1999) (1987), (12), 2637-42.*
Database Caplus Chemical Abstracts Service, Columbus, Ohio, US; Database Accession No. 1992:73028, Abstract of WO 2001087244 Nov. 22, 2001.*
Cainelli, G., et al., "Stereospecific Synthesis of a Chiral Intermediate for the Preparation of Thienamycin, Penems, and Carbapenems: Use of the Nitro Group as a Hydroxy Protecting Group", J. Chem. Soc. Perkin Trans. I, 1987, pp. 2637-2642.
International Searching Authority, English translation of Written Opinion (PCT/ISA/237) dated Jun. 8, 2010, issued in Application No. PCT/JP2010/057267.
WIPO, International Search Report, dated Jun. 8, 2010, issued in Application No. PCT/JP2010/057267.
WIPO, Written Opinion (PCT/ISA/237) dated Jun. 8, 2010, issued in Application No. PCT/JP2010/057267.
European Patent Office, extended European Search Report dated Aug. 23, 2012 issued in a counterpart European Patent Application No. 10767166.1.
European Patent Office, Office Action dated Mar. 21, 2013, issued in counterpart European Patent Application No. 10767166.1.

\* cited by examiner

*Primary Examiner* — Karl J Puttlitz
(74) *Attorney, Agent, or Firm* — Sughrue Mion, PLLC

(57) ABSTRACT

The present invention provides a cooling component or sensate component which has further strong cooling intensity and is excellent in the persistency or refresh-feeling and cool-feeling, a sensate composition comprising the same, and various products comprising the sensate composition. The present invention relates to, as a cooling component or sensate component, (3R)-1-menthyl 3-hydroxybutyrate represented by the following formula (I):

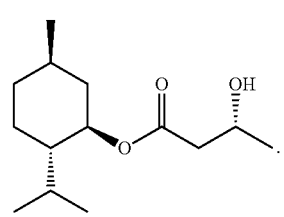

(I)

16 Claims, No Drawings

(3R)-L-MENTHYL 3-HYDROXYBUTYRATE, PROCESS FOR PRODUCING THE SAME, AND SENSATE COMPOSITION COMPRISING THE SAME

CROSS-REFERENCE TO RELATED APPLICATIONS

This application claims priority from Japanese Patent Application No. 2009-106605 filed on Apr. 24, 2009 and provisional U.S. patent application No. 61/232,550 filed on Aug. 10, 2009, the entire subject matter of which is incorporated herein by reference.

BACKGROUND OF THE INVENTION

1. Field of the Invention

The present invention relates to (3R)-1-menthyl 3-hydroxybutyrate and production method thereof and a sensate composition comprising the same. In addition, the invention relates to a flavor or fragrance composition, food or drink, fragrance or cosmetic, daily necessities and household goods, oral composition or pharmaceutical, which comprises the (3R)-1-menthyl 3-hydroxybutyrate or sensate composition.

2. Description of the Related Art

Up to now, cooling agents which exert a refreshing sense (refresh-feeling) or cool sense (cool-feeling), namely cooling effect, on human skin, oral cavity, nose and throat are used in dentifrices, sweets (e.g., chewing gum, candy and the like), tobacco, poultice, cosmetics and the like. As a flavoring substance which provides such a refresh-feeling or cool-feeling, 1-menthol (1-menthol) is now broadly used but its cooling effect has a weak point of lacking in persistency.

In addition to 1-menthol, a large number of compounds have been proposed and also used as the compound having cooling effect. In exemplifying the so far proposed compounds having cool-feeling effect other than 1-menthol, for example, 3-substituted-p-menthane (e.g., see JP-A-47-16647), N-substituted-p-menthane-3-carboxamide (e.g., see JP-A-47-16648), 1-menthyl glucoside (e.g., see JP-A-48-33069), 3-(1-menthoxy)propane-1,2-diol (e.g., see JP-A-58-88334), 1-menthyl 3-hydroxybutyrate (e.g., see JP-A-61-194049), 1-alkoxy-3-(1-menthoxy)propane-2-ol (e.g., see JP-A-2-290827), esters of 3-hydroxymethyl-p-menthane (e.g., see JP-A-5-255186), N-acetylglycinementhane methyl ester (e.g., see JP-A-5-255217), (−)-isopulegol (e.g., see JP-A-6-65023), (2S)-3-(1-menthoxy)propane-1,2-diol (e.g., see JP-A-7-82200), 2-hydroxymethylmenthol (e.g., see JP-A-7-118119) and the like can be mentioned.

SUMMARY OF THE INVENTION

As described in the above, 1-menthyl 3-hydroxybutyrate in which stereospecificity at the 3-position hydroxy group is not controlled has already been reported (cf. JP-A-61-194049) but its cooling intensity is not satisfactory yet, so that it is a universal theme to look closely into a compound which has further strong cooling intensity.

Accordingly, the invention provides a novel cooling component or sensate component which has further strong cooling intensity and is excellent in the persistency of refresh-feeling and cool-feeling.

Also, the invention provides a sensate composition which has further strong cooling intensity and is excellent in the persistency of refresh-feeling and cool-feeling.

In addition, the invention provides a flavor or fragrance composition, food or drink, fragrance or cosmetic, daily necessities and household goods, oral composition or pharmaceutical which comprises the aforementioned sensate composition.

With the aim of solving the above-mentioned problems, the inventors have conducted intensive studies and found that (3R)-1-menthyl 3-hydroxybutyrate represented by the formula (I)

[Chem. 1]

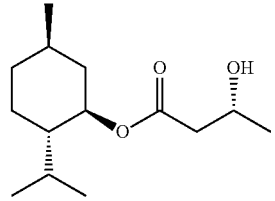

(I)

has further strong cooling intensity, is excellent in the persistency of cooling effect and is useful as a cooling component and sensate component, in comparison with the conventional 1-menthyl 3-hydroxybutyrate in which stereospecificity at the 3-position hydroxy group is not controlled (to be referred to as racemic body 1-menthyl 3-hydroxybutyrate hereinafter), and can alleviate the irritating smell possessed by 1-menthol when, for example, 1-menthol is used as the cooling agent, and further, in the case of a flavor or fragrance composition in which the (3R)-1-menthyl 3-hydroxybutyrate of the invention is added, odorous diffusivity and aroma remaining property of the flavor or fragrance composition are heightened and high odor quality improvement effect can be added to the products provided with the flavor or fragrance of said flavor or fragrance composition, and have accomplished the invention based on these findings.

Namely, the invention encompass the following embodiments.

[1] A cooling agent comprising (3R)-1-menthyl 3-hydroxybutyrate represented by the formula (I):

[Chem. 2]

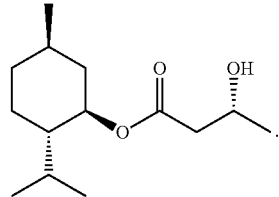

(I)

[2] The cooling agent according to [1], wherein an optical purity at the 3-position hydroxyl group of the (3R)-1-menthyl 3-hydroxybutyrate is 50% e.e. or more.

[3] A sensate composition comprising: (3R)-1-menthyl 3-hydroxybutyrate represented by the formula (I); and at least one component selected from the group consisting of a cooling component other than the (3R)-1-menthyl 3-hydroxybutyrate and a warming component.

[4] The sensate composition according to [3], wherein an optical purity at the 3-position hydroxyl group of the (3R)-1-menthyl 3-hydroxybutyrate is 50% e.e. or more.

[5] The sensate composition according to [3] or [4], wherein the cooling component other than the (3R)-1-menthyl 3-hydroxybutyrate is at least one component selected from the group consisting of menthol, menthone, camphor, pulegol, isopulegol, cineol, mint oil, peppermint oil, spearmint oil, eucalyptus oil, 3-1-menthoxypropane-1,2-diol, N-alkyl-p-menthane-3-carboxamide, 3-1-menthoxy-2-methylpropane-1,2-diol, p-menthane-3,8-diol, 2-1-menthoxyethanol, 3-1-menthoxypropanol, 1-menthyl lactate, menthone glycerol ketal, menthyl succinate, menthyl glutarate, dimenthyl glutarate and N-methyl-2,2-isopropylmethyl-3-methyl butanamide.

[6] The sensate composition according to [3] or [4], wherein the warming component is at least one component selected from the group consisting of vanillyl ethyl ether, vanillyl propyl ether, vanillin propylene glycol acetal, ethyl vanillin propylene glycol acetal, capsaicin, gingerol, vanillyl butyl ether, 4-(1-menthoxymethyl)-2-phenyl-1,3-dioxolan, 4-(1-menthoxymethyl)-2-(3',4'-dihydroxyphenyl)-1,3-dioxolan, 4-(1-menthoxymethyl)-2-(2'-hydroxy-3'-methoxyphenyl)-1,3-dioxolan, 4-(1-menthoxy-methyl)-2-(4'-methoxyphenyl)-1,3-dioxolan, 4-(1-menthoxymethyl)-2-(3',4'-methylenedioxyphenyl)-1,3-dioxolan, 4-(1-methoxymethyl)-2-(3'-methoxy-4'-hydroxyphenyl)-1,3-dioxolan, vanillin acetals, red pepper oil, red pepper oleoresin, ginger oleoresin, nonylic acid vanillylamide, jambu oleoresin, Japanese pepper extract, sanshool-I, sanshool-II, sanshoamide, black pepper extract, chavicine, piperine and spilanthol.

[7] A flavor or fragrance composition comprising (3R)-1-menthyl 3-hydroxybutyrate represented by the formula (I) in an amount of 0.001 to 90 weight % based on the total amount of the flavor or fragrance composition.

[8] The flavor or fragrance composition according to [7], wherein an optical purity at the 3-position hydroxyl group of the (3R)-1-menthyl 3-hydroxybutyrate is 50% e.e. or more.

[9] A product comprising (3R)-1-menthyl 3-hydroxybutyrate represented by the formula (I) in an amount of 0.0001 to 30 weight % based on the total amount of the product, wherein the product is selected from the group consisting of a food or drink, a fragrance or cosmetic, a daily necessities and household goods, an oral composition and a pharmaceutical.

[10] The product according to [9], wherein an optical purity at the 3-position hydroxyl group of the (3R)-1-menthyl 3-hydroxybutyrate is 50% e.e. or more.

[11] A flavor or fragrance composition comprising the sensate composition according to [3] or [4] in an amount of 0.001 to 90 weight % based on the total amount of the flavor or fragrance composition.

[12] A flavor or fragrance composition comprising the sensate composition according to [5] in an amount of 0.001 to 90 weight % based on the total amount of the flavor or fragrance composition.

[13] A flavor or fragrance composition comprising the sensate composition according to [6] in an amount of 0.001 to 90 weight % based on the total amount of the flavor or fragrance composition.

[14] A product comprising the sensate composition according to [3] or [4] in an amount of 0.0001 to 30 weight % based on the total amount of the product, wherein the product is selected from the group consisting of a food or drink, a fragrance or cosmetic, a daily necessities and household goods, an oral composition and a pharmaceutical.

[15] A product comprising the sensate composition according to [5] in an amount of 0.0001 to 30 weight % based on the total amount of the product, wherein the product is selected from the group consisting of a food or drink, a fragrance or cosmetic, a daily necessities and household goods, an oral composition and a pharmaceutical.

[16] A product comprising the sensate composition according to [6] in an amount of 0.0001 to 30 weight % based on the total amount of the product, wherein the product is selected from the group consisting of a food or drink, a fragrance or cosmetic, a daily necessities and household goods, an oral composition and a pharmaceutical.

[17] A method for producing (3R)-1-menthyl 3-hydroxybutyrate represented by the formula (I):

[Chem. 4]

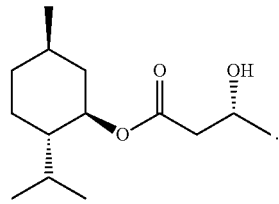

(I)

which comprises subjecting 1-menthyl acetoacetate represented by the formula (II) to asymmetric hydrogenation:

[Chem. 3]

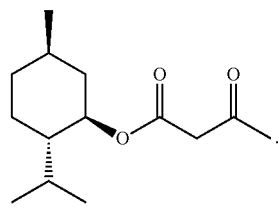

(II)

[18] The method for producing (3R)-1-menthyl 3-hydroxybutyrate according to [17], which comprises synthesizing the 1-menthyl acetoacetate by subjecting a mixture of 1-menthol and methyl acetoacetate to transesterification in the absence of a catalyst or in the presence of a protonic acid catalyst, and in the absence of a solvent or in an aliphatic hydrocarbon having 5 to 8 carbon atoms.

[19] A method for imparting a cooling sensation to a flavor or fragrance composition, a food or drink, a fragrance or cosmetic, a daily necessities and household goods, an oral composition or a pharmaceutical, which comprises adding (3R)-1-menthyl 3-hydroxybutyrate represented by the formula (I) to the flavor or fragrance composition, food or drink, fragrance or cosmetic, daily necessities and household goods, oral composition or pharmaceutical.

[20] The method according to [19], wherein an optical purity at the 3-position hydroxyl group of the (3R)-1-menthyl 3-hydroxybutyrate is 50% e.e. or more.

[21] (3R)-1-menthyl 3-hydroxybutyrate represented by the formula (I):

[Chem. 5]

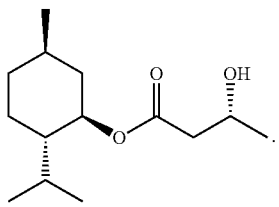

(I)

[Chem. 7]

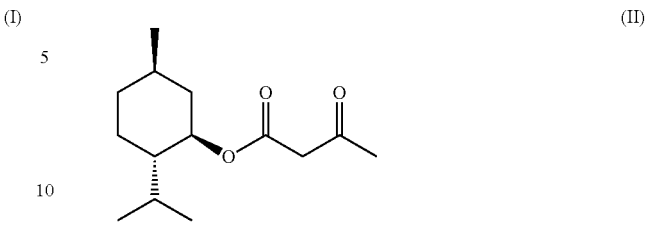

(II)

[22] The (3R)-1-menthyl 3-hydroxybutyrate according to [21], wherein an optical purity at the 3-position hydroxyl group of the (3R)-1-menthyl 3-hydroxybutyrate is 50% e.e. or more.

The (3R)-1-menthyl 3-hydroxybutyrate of the invention represented by the aforementioned formula (I) does not have a peculiar smell and the like, and when added in various food or drink, oral compositions, fragrances or cosmetics, daily necessities and household goodss, pharmaceutical and the like, it can add strong sense-stimulating effect such as refresh-feeling and cool-feeling to these products and also can add excellent refresh-feeling and cool-feeling having persistency thereto. Also, when (3R)-1-menthyl 3-hydroxybutyrate is used together with 1-menthol, it can alleviate the irritating smell possessed by 1-menthol. Further, (3R)-1-menthyl 3-hydroxybutyrate exerts an excellent characteristic of hardly generating skin irritation-feeling which is not desirable for human body and is excellent in stability because it does not develop color during storage.

In addition, the (3R)-1-menthyl 3-hydroxybutyrate of the invention represented by the aforementioned formula (I) has a particularly strong cooling intensity in comparison with 1-menthyl 3-hydroxybutyrate in which the stereospecificity of the 3-position hydroxyl group is not controlled.

DETAILED DESCRIPTION OF THE INVENTION

The following describes embodiments of the invention in detail.

In the invention, "(3R)-1-menthyl 3-hydroxybutyrate-"means (3R)-1-menthyl 3-hydroxybutyrate having an optical purity of more than 0% e.e. to 100% e.e. at the 3-position hydroxyl group.

The (3R)-1-menthyl 3-hydroxybutyrate of the invention represented by the following formula (I)

[Chem. 6]

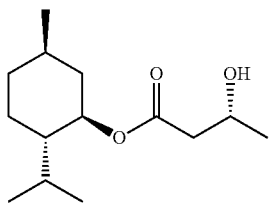

(I)

can be synthesized by subjecting 1-menthyl acetoacetate represented by the following formula (II)

to symmetric hydrogenation.

Regarding the 1-menthyl acetoacetate represented by the above-mentioned formula (II), several synthesis methods have so far been reported. For example, in JP-A-61-194049, its synthesis is carried out by allowing menthol and diketene to undergo transesterification in the presence of a weak base such as sodium acetate, but diketene has a problem of safety in industrially handling it because it has not only strong tearing property and toxicity but also explosive property.

Also, in the specification of U.S. Patent Application No. 2008/0175800, there is described a method for obtaining 1-menthyl acetoacetate by carrying out transesterification reaction of a mixture of 1-menthol and methyl acetoacetate or ethyl acetoacetate, without a solvent or in aprotic solvent such as ether, methylene chloride, tetrahydrofuran or toluene in the presence of Lewis acid such as zinc chloride, tin(IV) chloride or iron(IV) chloride and transesterification catalyst such as pyridine, imidazole or DMAP, but when these aprotic solvents are used, the methanol or ethanol formed by this exchange reaction is dissolved in the solvent and cannot therefore be removed so that it is not efficient for completing this transesterification in terms of chemical equilibrium.

Further, in order to remove the Lewis acid used at the time of completing the reaction, washing with a strong acid becomes essential, thus causing increase of the number of steps including subsequent neutralization and the like. In addition, when this Lewis acid is not removed at the time of distillation, it is inevitable to cause generation of an acidic gas, coloring of the distillation product and increase of impurities, as well as adhesion of an unusual smell.

In the invention, this esterification reaction can be carried out by heating a mixture of 1-menthol and methyl acetoacetate without a solvent or in an aliphatic hydrocarbon having 5 to 8 carbon atoms in the absence of a catalyst or in the presence of a proton acid catalyst, thereby effecting transesterification, and according to this method, 1-menthyl acetoacetate can be obtained almost quantitatively.

It is desirable to carry out this transesterification reaction at 50° C. or more, more desirably at 70° C. or more. As the aliphatic hydrocarbon having 5 to 8 carbon atoms, heptane, pentane, hexane, cyclohexane, substituted cyclohexane and the like are exemplified. Among them, it is desirable to use heptane, and substituted cyclohexane such as methyl cyclohexane, dimethyl cyclohexane and ethyl cyclohexane which has larger difference in boiling point with methanol and has broad utility.

The amount of the aliphatic hydrocarbon having 5 to 8 carbon atoms to be use is preferably from 0 to 30 times by weight, more preferably from 0.3 to 5 times by weight, based on menthol, and optimum heating temperature can be maintained by optionally adjusting this amount.

The amount of methyl acetoacetate to be used is preferably from 0.3 to 30 mol equivalent, more preferably from 1 to 10 mol equivalent, based on menthol.

When a proton acid catalyst is used as the catalyst in this transesterification reaction, an acidic substance which is used in general esterification reaction may be used, and illustratively, for example, sulfuric acid and sulfonic acids such as sulfuric acid, methanesulfonic acid, benzenesulfonic acid, p-toluenesulfonic acid, naphthalenesulfonic acid, camphorsulfonic acid, sulfonic acid-based ion exchange resin and acidic sodium sulfate; perhalogenoacetic acid such as trifluoroacetic acid and trichloroacetic acid, phosphoric acid and the like can be mentioned. As the desirable acidic substance, for example, sulfuric acid, methanesulfonic acid, p-toluenesulfonic acid, camphorsulfonic acid and the like can be exemplified, though not particularly limited to these. Among them, sulfuric acid, p-toluenesulfonic acid and the like are more desirable because they have versatility and can show high reaction yield. These proton acids can be used alone or by mixing two or more kinds, but it is desirable to use one kind. Amount of the proton acid catalyst which can be used in this transesterification reaction is generally from 0.001 to 20% by weight, preferably from 0.1 to 5% by weight, based on menthol.

The reaction temperature of this transesterification reaction is from 70° C. to 180° C., preferably from 80° C. to 120° C., and optional temperature can be maintained within this range by adjusting the amount of aliphatic hydrocarbon having 5 to 8 carbon atoms as the solvent. In addition, it is also possible to adjust the reaction temperature by changing pressure in the system.

The reaction time can be suitably adjusted depending on the reaction temperature or pressure, but it is preferred to complete the reaction usually within 40 hours, preferably within 30 hours, more preferably 1 to 24 hours, from the economical point of view.

After completion of the reaction, in the case of using the proton acid catalyst, 1-menthyl acetoacetate can be obtained by distillation generally after carrying out a neutralization treatment and, if needed, evaporating the solvent to perform distillation. According to the neutralization treatment in this case, when a catalytically effective amount of a proton acid is used, said proton acid may be removed from the system by washing with a basic aqueous solution in an amount sufficient enough for inactivating the proton acid, or it may be kept inside the system by forming its salt through the addition of a basic substance in an amount sufficient enough for inactivating the proton acid. As the basic aqueous solution which inactivates proton acid, an aqueous solution of sodium hydroxide, calcium hydroxide, sodium carbonate, sodium hydrogen carbonate or the like can be exemplified, though not limited thereto. Also, as the basic substance which inactivates a proton acid, in addition to the aforementioned sodium hydroxide, calcium hydroxide, sodium carbonate, sodium hydrogen carbonate and the like, organic amines which can form stable salts with said proton acid, such as triethylamine, diethylamine and ammonia and the like can be mentioned, but the basic substances which inactivate proton acid are not particularly limited thereto.

As described in the above, it is desirable to carry out synthesis of the 1-menthyl acetoacetate represented by the formula (II) by a method in which transesterification reaction of 1-menthol and methyl acetoacetate is carried out without solvent or in an aliphatic hydrocarbon having 5 to 8 carbon atoms, and without catalyst or in the presence of a proton acid catalyst.

As described in the above, according to the invention, the (3R)-1-menthyl 3-hydroxybutyrate of interest can be synthesized by subjecting the 1-menthyl acetoacetate represented by the following formula (II):

[Chem. 8]

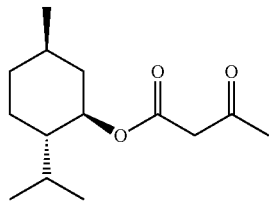

(II)

to asymmetric hydrogenation.

As the asymmetric hydrogenation method, for example, there can be mentioned a method in which 1-menthyl acetoacetate represented by the above-mentioned formula (II) as a starting substance is subjected to asymmetric hydrogenation without solvent or in a solvent in the presence of a ruthenium complex which uses R-form of the optically active ruthenium complex described in JP-A-11-302226 or JP-A-2002-037760 (herein incorporated by reference), such as R-form of the optically active tertiary diphosphine compound represented by the following formula (III), as the ligand.

[Chem. 9]

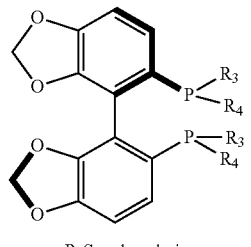

R-Segphos deriv (III)

(In the formula, $R^3$ and $R^4$ each independently represent a cycloalkyl group, an unsubstituted or substituted phenyl group or a five-membered aromatic heterocyclic ring residue.)

As the ruthenium complex which uses R-form of the optically active tertiary diphosphine compound represented by the above-mentioned formula (III) as the ligand, for example, there may be mentioned the ruthenium complexes represented by the following formulae (IV) to (IX) (in the formulae, X represents a halogen atom, L represents an optically active tertiary phosphine ligand (R-form), A represents a tertiary amine, ARENE represents benzene ring which may have a substituent group, G represents a halogen atom or acetoxy group, J represents $BF_4$, $ClO_4$, $PF_6$ or $BPh_4$ (Ph represents phenyl group), Q represents hydrogen, a lower alkyl group, phenyl group which may have a substituent group or benzyl group which may have a substituent group, n is an integer of from 1 to 3, and DMF represents N,N-dimethylformamide).

| | |
|---|---|
| $[Ru_2X_4(L)_2](A)$ | (IV) |
| $[RuX(ARENE)(L)]X$ | (V) |
| $[Ru(G)_2(L)]$ | (VI) |
| $[Ru(L)](J)_2$ | (VII) |
| $[\{RuX(L)\}_2(\mu\text{-}X)_3][NH_2Q_2]$ | (VIII) |
| $RuX_2(L)(DMF)_n$ | (IX) |

As examples of the above-mentioned complexes, there may be mentioned, for example,

[Ru$_2$Cl$_4$(SEGPHOS)$_2$](NEt$_3$) [SEGPHOS is [4,4'-bis-1,3-benzodioxole]-5,5'-diylbis(diphenylphosphine), Et is ethyl group],
[Ru$_2$Cl$_4$(p-Tol-SEGPHOS)$_2$](NEt$_3$) [p-Tol-SEGPHOS is [4,4'-bis-1,3-benzodioxole]-5,5'-diylbis(di-p-tolylphosphine]],
[Ru$_2$Cl$_4$(DM-SEGPHOS)$_2$](NEt$_3$) [DM-SEGPHOS is [4,4'-bis-1,3-benzodioxole]-5,5'-diylbis[di-3,5-dimethylphenylphosphine]],
[RuCl(C$_6$H$_6$)(SEGPHOS)]Cl,
[RuBr(C$_6$H$_6$)(SEGPHOS)]Br,
[RuI(C$_6$H$_6$)(SEGPHOS)]I,
[RuCl(p-cymene)(SEGPHOS)]Cl,
[RuBr(p-cymene)(SEGPHOS)]Br,
[RuI(p-cymene)(SEGPHOS)]I,
[RuCl(C$_6$H$_6$)(p-Tol-SEGPHOS)]Cl,
[RuBr(C$_6$H$_6$)(p-Tol-SEGPHOS)]Br,
[RuI(C$_6$H$_6$)(p-Tol-SEGPHOS)]I,
[RuCl(p-cymene)(p-Tol-SEGPHOS)]Cl,
[RuBr(p-cymene)(p-Tol-SEGPHOS)]Br,
[RuI(p-cymene)(p-Tol-SEGPHOS)]I,
[RuCl(C$_6$H$_6$)(DM-SEGPHOS)]Cl,
[RuBr(C$_6$H$_6$)(DM-SEGPHOS)]Br,
[RuI(C$_6$H$_6$)(DM-SEGPHOS)]I,
[RuCl(p-cymene)(DM-SEGPHOS)]Cl,
[RuBr(p-cymene)(DM-SEGPHOS)]Br,
[RuI(p-cymene)(DM-SEGPHOS)]I,
[Ru(OAc)$_2$(SEGPHOS)] [OAc is acetoxy group],
[Ru(OAc)$_2$(p-Tol-SEGPHOS)],
[Ru(OAc)$_2$(DM-SEGPHOS)],
[RuBr$_2$(SEGPHOS)],
[RuBr$_2$(p-Tol-SEGPHOS)],
[RuBr$_2$(DM-SEGPHOS)],
[Ru(SEGPHOS)](BF$_4$)$_2$,
[Ru(SEGPHOS)](ClO$_4$)$_2$,
[Ru(SEGPHOS)](PF$_6$)$_2$,
[Ru(p-Tol-SEGPHOS)](BF$_4$)$_2$,
[Ru(p-Tol-SEGPHOS)](ClO$_4$)$_2$,
[Ru(p-Tol-SEGPHOS)](PF$_6$)$_2$,
[Ru(DM-SEGPHOS)](BF$_4$)$_2$,
[Ru(DM-SEGPHOS)](ClO$_4$)$_2$,
[Ru(DM-SEGPHOS)](PF$_6$)$_2$,
[{RuCl(SEGPHOS)}$_2$(μ-Cl)$_3$][NH$_2$Me$_2$][Me is methyl group],
[{RuCl(SEGPHOS)}$_2$(μ-Cl)$_3$][NH$_2$Et$_2$],
[{RuCl(p-Tol-SEGPHOS)}$_2$(μ-Cl)$_3$][NH$_2$Me$_2$],
[{RuCl(p-Tol-SEGPHOS)}$_2$(μ-Cl)$_3$][NH$_2$Et$_2$],
[{RuCl(DM-SEGPHOS)}$_2$(μ-Cl)$_3$][NH$_2$Me$_2$],
[{RuCl(DM-SEGPHOS)}$_2$(μ-Cl)$_3$][NH$_2$Et$_2$],
RuCl$_2$(SEGPHOS)(DMF)$_n$[DMF is N,N-dimethylformamide],
RuCl$_2$(p-Tol-SEGPHOS)(DMF)$_n$,
RuCl$_2$(DM-SEGPHOS)(DMF)$_n$,
and the like.

Also, as the solvent, protic solvent such as methanol, ethanol and isopropyl alcohol are suitable, and mixed solvents of the solvent with tetrahydrofuran, toluene, benzene, methyl acetate, ethyl acetate, methylene chloride and the like are also suitable. In addition, it is more desirable that 1-menthyl acetoacetate is allowed to undergo the asymmetric hydrogenation after dissolving it in the above-mentioned solvent.

The asymmetric hydrogenation suitably progresses when the ruthenium complex to be present in the solvent is added in an amount of from 1/100 to 1/100,000 times by mol, more preferably from 1/1,000 to 1/50,000 times by mol, based on 1-menthyl acetoacetate. In this case, the asymmetric hydrogenation is carried out by setting the hydrogen pressure to a level of from 0.1 to 10 MPa, more preferably from 1 to 5 MPa, and the asymmetric hydrogenation temperature to a level of from 0 to 150° C., more preferably from 20 to 100° C., and stirring for a period of from 1 to 48 hours.

In addition, according to the invention, selectivity and reaction conversion ratio of the starting substance, 1-menthyl acetoacetate, can be improved by carrying out the asymmetric hydrogenation in the presence of an acid. As the suitable acid, mineral acids such as sulfuric acid or organic acids such as methanesulfonic acid, p-toluenesulfonic acid and benzenesulfonic acid can be exemplified. In this case, it is desirable to add the acid in an amount of from 0.5 to 10 mol equivalent, preferably from 0.7 to 8 mol equivalent, further preferably from 0.9 to 5 mol equivalent, based on the ruthenium complex.

After completion of the asymmetric hydrogenation in this manner, a purification treatment operation may be carried out in the usual way. That is, a method in which the solvent is evaporated and then the resulting residue is distilled under a reduced pressure and a method in which the product is purified by a silica gel column chromatography can be employed. By such methods, the (3R)-1-menthyl 3-hydroxybutyrate of interest can be produced with high selectivity and high yield.

The novel (3R)-1-menthyl 3-hydroxybutyrate of the invention represented by the formula (I) obtained in this manner is markedly strong in the cooling intensity, has persistent cooling effect and can be used alone directly as a cooling agent or sensate agent. However, since this effect is considerably depending on the optical purity at the 3-position hydroxyl group of (3R)-1-menthyl 3-hydroxybutyrate, its cooling intensity is markedly strong and the persistent cooling effect can be actually felt when the optical purity is 50% e.e. or more, in comparison with its racemic body 1-menthyl 3-hydroxybutyrate, and the difference can be felt more clearly when it is 70% e.e. When the optical purity is 90% e.e. or more, it can be felt that the product is an excellent cooling agent or sensate agent having the aforementioned characteristics, which is considerably different from the racemic body 1-menthyl 3-hydroxybutyrate. On the contrary, when the optical purity at the 3-position hydroxyl group is less than 50% e.e., difference in its effect from racemic body 1-menthyl 3-hydroxybutyrate may become small so that its effectiveness as an optically active body may become low. That is, regarding the optical purity at the 3-position hydroxyl group, 50% e.e. or more is desirable, 70% e.e. or more is more desirable and 90% e.e. or more is further desirable.

The (3R)-1-menthyl 3-hydroxybutyrate of the invention can be added in a product such as a food or drink, a cosmetic or fragrance, a daily necessities and household goods, an oral composition and a pharmaceutical. It is necessary to change application range and application method thereof optionally, depending on the kind and application purpose of the product, but in general, it is desirable to use it at a concentration of from 0.0001 to 30% by weight, particularly from 0.01 to 20% by weight, based on the total composition of the product. Examples of the products are similar to that of the product described below.

The (3R)-1-menthyl 3-hydroxybutyrate of the invention can be added in a flavor or fragrance composition. It is necessary to change application range and application method thereof optionally, depending on the kind and application purpose of the flavor or fragrance composition, but in general, it is desirable to use it at a concentration of from 0.001 to 90% by weight, particularly from 0.01 to 50% by weight, based on the total composition of the flavor or fragrance composition.

The sensate composition can be prepared by using the (3R)-1-menthyl 3-hydroxybutyrate of the invention together with at least one kind of cooling components selected from a cooling component other than the (3R)-1-menthyl 3-hydroxybutyrate and/or at least one kind of warming components.

In this connection, the sensate stimulation according to the invention is an effect to stimulate a sense. The aforementioned effect to stimulate a sense includes cooling effect and warming effect, and according to the invention therefore, the sensate composition is used as a general idea of including a cooling composition and a warming composition.

As the aforementioned cooling component other than the (3R)-1-menthyl 3-hydroxybutyrate of the invention, for example, menthol, menthone, camphor, pulegol, isopulegol, cineol, mint oil, peppermint oil, spearmint oil, eucalyptus oil, 3-1-menthoxypropane-1,2-diol, N-alkyl-p-menthane-3-carboxamide, 3-1-menthoxy-2-methylpropane-1,2-diol, p-menthane-3,8-diol, 2-1-menthoxyethanol, 3-1-menthoxypropanol, 1-menthyl lactate, menthone glycerin ketal, menthyl succinate, menthyl glutarate, dimenthyl glutarate and N-methyl-2,2-isopropylmethyl-3-methyl butanamide and the like can be exemplified. These can be used alone or by optionally blending two or more kinds.

As the warming component, there may be mentioned vanillyl ethyl ether, vanillyl propyl ether, vanillin propylene glycol acetal, ethyl vanillin propylene glycol acetal, capsaicin, gingerol, vanillyl butyl ether, 4-(1-menthoxymethyl)-2-phenyl-1,3-dioxolan, 4-(1-menthoxymethyl)-2-(3',4'-dihydroxyphenyl)-1,3-dioxolan, 4-(1-menthoxymethyl)-2-(2'-hydroxy-3'-methoxyphenyl)-1,3-dioxolan, 4-(1-menthoxy-methyl)-2-(4'methoxyphenyl)-1,3-dioxolan, 4-(1-menthoxymethyl)-2-(3',4'-methylenedioxyphenyl)-1,3-dioxolan, 4-(1-methoxymethyl)-2-(3'-methoxy-4'-hydroxyphenyl)-1,3-dioxolan, vanillin acetals, red pepper oil, red pepper oleoresin, ginger oleoresin, nonylic acid vanillylamide, jambu oleoresin, Japanese pepper extract, sanshool-I, sanshool-II, sanshoamide, black pepper extract, chavicine, piperine, spilanthol and the like. These may be used alone or by optionally blending two or more of them.

The sensate composition comprising the (3R)-1-menthyl 3-hydroxybutyrate of the invention and at least one kind of cooling components other than the (3R)-1-menthyl 3-hydroxybutyrate is described below.

When the sensate composition comprising the (3R)-1-menthyl 3-hydroxybutyrate of the invention and a cooling component other than this is prepared, the (3R)-1-menthyl 3-hydroxybutyrate of the invention and the cooling component other than this can be used at an optional ratio within such a range that the effect of the invention is not spoiled, but it is desirable that the application ratio of the (3R)-1-menthyl 3-hydroxybutyrate and the cooling component other than this is within the range of from 1:99 to 95:5 by a weight ratio.

In addition, the sensate composition described in the above has a strong and persistent cooling effect, and is a sensate composition having increased cooling intensity.

The sensate composition comprising the (3R)-1-menthyl 3-hydroxybutyrate of the invention and a warming component, and further sensate composition comprising the (3R)-1-menthyl 3-hydroxybutyrate, a cooling component other than the (3R)-1-menthyl 3-hydroxybutyrate and a warming component are described below.

When the (3R)-1-menthyl 3-hydroxybutyrate of the invention is used together with the warming component, either of cooling effect or warming effect is exerted depending on the blending ratio of the total of the (3R)-1-menthyl 3-hydroxybutyrate and cooling component other than this, which are the cooling components in the sensate composition, and the warming component. Thus, the sense stimulating effect of the sensate composition can be controlled by the above blending ratio.

(1) The blending ratio of the (3R)-1-menthyl 3-hydroxybutyrate and the warming component in the sensate composition comprising the (3R)-1-menthyl 3-hydroxybutyrate and at least one kind of warming components is described below.

In case that cooling effect is intended, it may be within such a range that warming effect of the warming component is not added by the blending of the warming component, and in general, the blending amount is from 0.001 to 0.95 times by weight, preferably from 0.003 to 0.5 times by weight, based on the weight of the (3R)-1-menthyl 3-hydroxybutyrate. In this case, in the sensate composition of the invention, further improvement of cooling effect can be achieved and cooling effect is increased by the addition of the warming component to the (3R)-1-menthyl 3-hydroxybutyrate at the above-mentioned ratio.

In addition, in case that warming effect is intended, the (3R)-1-menthyl 3-hydroxybutyrate may be within such a range that cooling effect is not added by the blending of the (3R)-1-menthyl 3-hydroxybutyrate, and in general, the blending amount is from 0.001 to 0.95 times by weight, preferably from 0.01 to 0.5 times by weight, based on the total weight of the warming component.

(2) The blending ratio of the total weight of the (3R)-1-menthyl 3-hydroxybutyrate and cooling component other than this and the warming component in the sensate composition comprising the (3R)-1-menthyl 3-hydroxybutyrate, the cooling component other than this and at least one kind of warming components is described below.

In case that cooling effect is intended, it may be within such a range that warming effect of the warming component is not added by the blending of the warming component, and in general, the blending amount is from 0.001 to 0.95 times by weight, preferably from 0.003 to 0.5 times by weight, based on the total weight of the (3R)-1-menthyl 3-hydroxybutyrate and cooling component other that this. In this case, in the sensate composition of the invention, further improvement of cooling effect can be achieved and cooling effect is increased by the addition of the warming component to the (3R)-1-menthyl 3-hydroxybutyrate and cooling component other than this at the above-mentioned ratio.

In addition, in case that warming effect is intended, the total weight of the (3R)-1-menthyl 3-hydroxybutyrate and cooling component other than this may be within such a range that cooling effect is not added by the blending of the (3R)-1-menthyl 3-hydroxybutyrate and cooling component other than this, and in general, the blending amount is from 0.001 to 0.95 times by weight, preferably from 0.01 to 0.5 times by weight, based on the total weight of the warming component.

The sensate composition of the present invention can be added in a flavor or fragrance composition, a food or drink, a cosmetic or flagrance, a daily necessities and household goods, an oral composition or a pharmaceutical.

According to the invention, the above-mentioned sensate composition may be directly added in various products such as a food or drink, a fragrance or cosmetic, a daily necessities and household goods, an oral composition and a pharmaceutical, or the above-mentioned sensate composition may be firstly added in a flavor or fragrance composition to make a sensate composition-containing flavor or fragrance composition (flavor or fragrance composition of the invention), and this sensate composition-containing flavor or fragrance composition can be blended with a product. In that case, by adding (3R)-1-menthyl 3-hydroxybutyrate, cooling component other than this and warming component to separate flavor or fragrance compositions, the respective flavor or fragrance compositions may be mixed with a product.

According to the flavor or fragrance composition of the invention, various synthetic aromachemical, natural essential oil, synthetic essential oil, citrus oil, animal aromachemical and the like can be mentioned as the flavor or fragrance components which can be contained together with the (3R)-1-menthyl 3-hydroxybutyrate or sensate composition, and a broad range of flavor or fragrance components described for example in "Shuchi Kanyo Gijutsu Shu (Koryo) Daiichibu (Known/Common Technical Book (Flavor or Fragrances) Part I)" (Jan. 29, 1999, published by the Japanese Patent Office), herein incorporated by reference, can be used. As typical ones among them, for example, α-pinene, limonene, neral, geranial, 2,5-dimethyl-4-hydroxy-3(2H)-furanone, vanillin, ethylvanillin, geraniol, nerol, citronellol, cis-3-hexenol, phenylethyl alcohol, styralyl acetate, eugenol, rose oxide, linalool, benzaldehyde, muscone, Musk T (manufactured by Takasago International Corp.), Thesaron (manufactured by Takasago International Corp.) and the like can be cited.

The content of the sensate composition in the sensate composition-containing flavor or fragrance composition of the invention can be adjusted based on the kinds of the flavor or fragrance or other components to be mixed together, application purpose of the flavor or fragrance composition and the like. For example, in the case of a flavor or fragrance composition for fragrance or cosmetic use, the content of the sensate composition is generally from 0.001 to 90% by weight, preferably from 0.001 to 70% by weight, particularly preferably from 0.01 to 50% by weight, based on the total weight of the flavor or fragrance composition.

In addition, in the case of a flavor or fragrance composition for food or drink use, the content of the sensate composition is preferably from 0.001 to 90% by weight, more preferably from 0.01 to 50% by weight, based on the total weight of the flavor or fragrance composition. Further, the same content is desirable also in the case of the flavor or fragrance composition for daily necessities and household goods, oral composition or pharmaceutical use.

As occasion demands, the flavor or fragrance composition of the invention which contains the (3R)-1-menthyl 3-hydroxybutyrate or sensate composition may contain one or two or more fragrance retainers generally used in flavor or fragrance compositions. As the fragrance retainers in that case, for example, ethylene glycol, propylene glycol, dipropylene glycol, glycerin, hexyl glycol, benzyl benzoate, triethyl citrate, diethyl phthalate, hercholine, medium chain fatty acid triglyceride, medium chain fatty acid diglyceride and the like can be mentioned, and one or two or more thereof can be contained.

As described in the above, the sensate composition of the invention can be used for adding sensory stimulus such as cool-feeling to various products, with the sensate composition itself or by making it into a flavor or fragrance composition which contains the sensate composition. As the products to which sensory stimulus such as cool-feeling can be added with the sensate composition itself of the invention or with the flavor or fragrance composition which contains the sensate composition, for example, a food or drink, a fragrance or cosmetic, a daily necessities and household goods, an oral composition, a pharmaceutical and the like can be mentioned.

As illustrative examples of the food or drink to which sensory stimulus such as cool-feeling can be added with the sensate composition of the invention or the sensate composition-containing flavor or fragrance composition which contains the same, there may be mentioned drinks such as fruit juice drinks, fruit wines, milk drinks, carbonated drink, soft drink and drink preparations; ices such as ice creams, sherbets and ice candies; desserts such as jelly and pudding; Western style cakes such as cake, cookie, chocolate and chewing gum, Japanese style confections such as bean-jam bun, sweet beans jelly and Uiro; jams; candies; breads; tea drinks or luxury drinks such as green tea, Oolong tea, black tea, persimmon leaf tea, chamomile tea, low striped bamboo tea, mulberry tea, dokudami tea, Pu-erh tea, mate tea, Rooibos tea, Gymnema tea, Guava tea, coffee and cocoa; soups such as Japanese style soup, Western style soup and Chinese soup ; flavoring and seasoning; various instant drinks or convenience foods; various snack foods and the like, though not limited thereto.

In addition, as the fragrance or cosmetic, or daily necessities and household goods, to which sensory stimulus such as cool-feeling can be added with the sensate composition of the invention or the sensate composition-containing flavor or fragrance composition which contains the same, there may be mentioned, for example, fragrance products, foundation cosmetics, finishing cosmetics, hair cosmetics, suntan cosmetics, medicated cosmetics, hair care products, soap, body washers, bath agents, cleansers, soft finishing agents, detergents, kitchen cleaners, bleachers, aerosols, deodorants or aromatics, repellents, cigarette products, other household goods and the like.

More illustratively,
as the fragrance products, perfume, eau de perfume, eau de toilette, eau de cologne and the like;
as the foundation cosmetics, cleansing cream, banishing cream, cleansing cream, cold cream, massage cream, milky lotion, skin lotion, beauty lotion, pack, makeup remover and the like;
as the finishing cosmetics, foundation, face powder, solid face powder, talcum powder, rouge, lip barm, cheek rouge, eye liner, mascara, eye shadow, eyebrow pencil, eye pack, nail enamel, enamel remover and the like; and
as the hair cosmetics, pomade, brilliantine, set lotion, hair stick, hair solid, hair oil, hair treatment, hair cream, hair tonic, hair liquid, hair spray, bandrine, revitalizing hair tonic, hair dye and the like; can be mentioned.
As the suntan cosmetics, suntan products, sunscreen product and the like;
as the medicated cosmetics, antiperspirant, after shaving lotion or gel, permanent wave agent, medicated soap, medicated shampoo, medicated skin cosmetics and the like;
as the hair care products, shampoo, rinse, rinse-in-shampoo, conditioner, treatment, hair pack and the like;
as the soap, toilet soap, bath soap, perfume soap, transparent soap, synthetic soap and the like;
as the body washers, body soap, body shampoo, hand soap and the like;
as the bath agents, bathing agents (bath salt, bath tablet, bath liquid and the like), foam bath (bubble bath and the like), bath oil (bath perfume, bath capsule and the like), milk bath, bath jelly, bath cube and the like; and
as the detergents, heavy detergent for clothing use, light detergent for clothing use, liquid detergent, washing soap, compact detergent, powder soap and the like; can be mentioned.
As the soft finishing agents, softener, furniture care and the like;

as the cleaners, cleanser, house cleaner, toilet cleaner, bath cleaner, glass cleaner, mildew remover, cleaner for drainpipe use and the like;

as the kitchen cleaners, kitchen soap, kitchen synthetic soap, tableware cleaner and the like;

as the bleachers, oxidation type bleacher (chlorine type bleacher, oxygen type bleacher and the like), reduction type bleacher (sulfur type bleacher and the like), optical bleacher and the like;

as the aerosols, spray type, powder spray and the like;

as the deodorants or aromatics, solid type, gel type, liquid type and the like; and as the household goods, tissue paper, toilet paper and the like; can be mentioned.

As the oral composition, for example, dentifrice, oral cavity cleaner, mouth wash, troche, chewing gums and the like; and as the pharmaceuticals, skin external preparations such as poultices and ointment, internal medicines and the like; can be mentioned.

When the sensate composition of the invention or the sensate composition-containing flavor or fragrance composition containing the same are used for giving sensory stimulus such as cool-feeling to the above-mentioned various products, the sensate composition or the sensate composition-containing flavor or fragrance composition containing the same may be added or given directly as such to a product in response to the kinds or final shape (e.g., product shapes such as liquid, solid, powder, gel, mist and aerosol) of the product to which sensory stimulus such as cool-feeling is given; the sensate composition or the sensate composition-containing flavor or fragrance composition containing the same may be added or given thereto in a liquid state by dissolving, for example, in polyhydric alcohols such as alcohols, propylene glycol or glycerol; may be added or given thereto in a solubilized or dispersed state by dissolving or emulsion-dispersing using natural gummy matters such as gum arabic and tragacanth gum, and surfactants (e.g., nonionic surfactant such as a glycerin fatty acid ester and sucrose fatty acid ester, an anionic surfactant, a cationic surfactant, an ampholytic surfactant and the like); may be added or given in a powdery state by forming a coat using natural gummy matters such as gum arabic or fillers such as gelatin and dextrin; or may be added or given as microcapsules by treating with an encapsulation agent. In addition, by including into inclusion compounds such as cyclodextrin, the sensate composition and the sensate composition-containing flavor or fragrance composition containing the same may be stabilized and also used as sustained release products.

Amount of the sensate composition to be added or given to various products in carrying out provision of sensory stimulus such as cool-feeling can be adjusted in response to the kind or shape of each product, the sensory stimulus such as cool-feeling providing effect required for the product, and the like. In general, it is desirable that the adding amount or giving amount of the sensate composition is from 0.0001 to 30% by weight, more desirably from 0.01 to 20% by weight, based on the weight of each product.

EXAMPLES

The following illustratively describes the invention based on examples, but the invention is not limited to these examples which may be optionally changed within such a range that the scope of the invention is not spoiled. In this connection, the apparatus, devices and the like used in the synthesis examples and examples for the verification and physical property measurement of the formed products are as follows.

$^1$H NMR: Bruker Japan DRX-500

IR: Nicolet AVATAR 360FT-IR

MS: Shimadzu Corp. GCMS-QP2010

Example 1

(1) Production of 1-menthyl acetoacetate

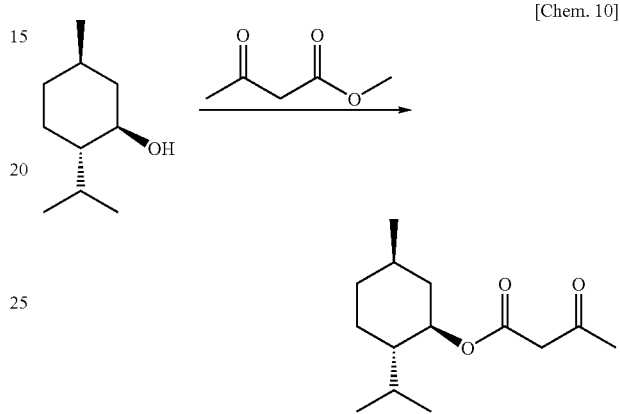

[Chem. 10]

100.0 g (0.64 mol) of 1-menthol, 81.7 g (0.70 mol) of methyl acetoacetate, 1.5 g of p-toluenesulfonic acid and 150 g of heptane were added to a 500 ml capacity three neck flask equipped with a thermometer, Dean-Sterk tube and Dimroth condenser, and heat under reflux was performed. The methanol formed during this period was removed by the Dean-Sterk tube, and menthol as a raw material disappeared 6 hours later.

The thus obtained reaction solution was washed with 30 ml of saturated sodium hydrogen carbonate aqueous solution and 30 ml of saturated saline in this order and then heptane was evaporated to carry out distillation under a reduced pressure (114 to 115° C./170 Pa), thereby obtaining 148.0 g of the intended 1-menthyl acetoacetate as a colorless oily substance (theoretical yield based on 1-menthol, 96.2%).

Physical Property Data (NMR, IR, MS)

$^1$H NMR (CDCl$_3$, 500 MHz): δ (ppm)=0.77 (d, 3H), 0.85 to 1.07 (m 9H), 1.38 (m, 1H), 1.50 (m, 1H), 1.66 to 1.71 (m, 2H), 1.87 (m, 1H), 2.02 (m, 1H), 2.27 (s, 3H), 3.43 (s, 2H), 4.74 (td, 1H).

IR (NaCl): 2956, 2870, 1718, 1647, 1453, 1412, 1362, 1313, 1242, 1180, 1150, 984 (cm$^{-1}$).

MS (m/e): 240 (M+1), 225, 197, 155, 141, 138, 123, 109, 95 (P), 81, 69, 43, 41.

(2) Production of (3R)-1-menthyl 3-hydroxybutyrate

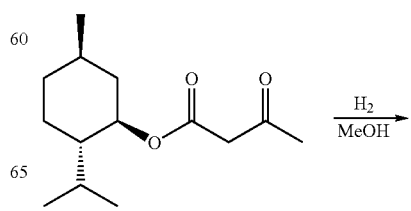

[Chem. 11]

-continued

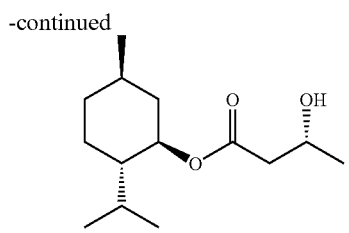

144.2 g (0.60 mol) of 1-menthyl acetoacetate, 98.8 mg (12.0 μmol) of a catalyst [{RuCl((R)-SEGPHOS)}$_2$(μ-Cl)$_3$][NH$_2$Me$_2$] and 75 ml of methanol were put into a 500 ml capacity autoclave and allowed to undergo the reaction at 70° C. for 5.5 hours under a hydrogen pressure of 4 MPa. The thus obtained reaction solution was subjected to evaporation of the solvent and then distilled under a reduced pressure (121° C./170 Pa) to obtain 143.1 g (yield 98.4%) of the (3R)-1-menthyl 3-hydroxybutyrate of interest as a colorless oily substance.

In this connection, the "SEGPHOS" in the above-mentioned catalyst means [4,4'-bis-1,3-benzodioxole]-5,5'-diyl-bis(diphenylphosphine).

Physical Property Data (NMR, IR, MS)

$^1$H NMR (CDCl$_3$, 500 MHz): δ (ppm)=0.76 (d, 3H), 0.88 to 1.08 (m, 9H), 1.22 (d, 3H), 1.38 (m, 1H), 1.51 (m, 1H), 1.66 to 1.70 (m, 2H), 1.85 (m, 1H), 1.98 (m, 1H), 2.41 (dd, 1H), 2.47 (dd, 1H), 3.12 (sd, 1H), 4.19 (m, 1H), 4.74 (td, 1H).

IR (NaCl): 3442, 2957, 2930, 2870, 1730, 1456, 1372, 1292, 1249, 1180, 1084, 984 (cm$^{-1}$).

MS (m/e): 243 (M+1), 227, 210, 199, 181, 155, 140, 138, 123, 105, 95 (P), 81, 69, 43, 41.

The optical purity of the (3R)-1-menthyl 3-hydroxybutyrate obtained in Example 1 at the 3-position hydroxyl group was analyzed by separating with high performance liquid chromatography, and the selectivity was 99.0% and calculated as 98.0% e.e.

Example 2

Comparative Sensory Evaluation of (3R)-1-menthyl 3-hydroxybutyrate and its Racemic Body A 50 ppm aqueous solution of each of the (3R)-1-menthyl 3-hydroxybutyrate obtained in Example 1 and its racemic body 1-menthyl 3-hydroxybutyrate was prepared. Oral sensory evaluation for the 50 ppm aqueous solutions was carried out by ten professional panels having 5 years or more of experience.

As a result, all of the ten panels answered that the (3R)-1-menthyl 3-hydroxybutyrate has stronger cool-feeling and superior refreshing nature.

Example 3

Synergistic Effect with Menthol

A sensate composition was prepared by mixing the (3R)-1-menthyl 3-hydroxybutyrate obtained in Example 1 with 1-menthol at a ratio of 1:9 (weight ratio). Oral sensory evaluation was carried out by preparing 1,000 ml of a 20 ppm aqueous solution of the thus obtained sensate composition, and the oral sensory evaluation was carried out also on a 20 ppm aqueous solution of 1-menthol alone as a comparison.

In this connection, the evaluation was carried out by ten professional panels having 5 years or more of experience, in which 10 ml of each of the above-mentioned aqueous solutions was kept in the mouth for 10 seconds and then spat out and, regarding this timing as 0 second, strength of its refreshing nature (refreshing feeling) at this timing and persistence of the strength of refreshing nature (refreshing feeling) 3 minutes thereafter were evaluated. Results of these are shown in Tables 1 and 2.

TABLE 1

Strength evaluation of refreshing nature

| Sensate composition | The mixture has stronger refreshing nature (refreshing feeling) | They has equivalent refreshing nature (refreshing feeling) | Menthol alone has stronger refreshing nature (refreshing feeling) |
|---|---|---|---|
| 1:9 Mixture | 8 | 1 | 1 |

TABLE 2

Strength persistency evaluation of refreshing nature

| Sensate composition | The mixture has stronger persisting feeling of refreshing nature | They has equivalent persisting feeling of refreshing nature | Menthol alone has stronger persisting feeling of refreshing nature |
|---|---|---|---|
| 1:9 Mixture | 10 | 0 | 0 |

As shown in Table 1, 8 of the 10 panels answered that the 1:9 mixture has stronger refreshing nature (refreshing feeling) in comparison with menthol alone.

Also, as shown in Table 2, all of the 10 panels answered that the 1:9 mixture has stronger persisting feeling of refreshing nature in comparison with menthol alone.

As is evident from Examples 2 and 3, it can be understood that the (3R)-1-menthyl 3-hydroxybutyrate of the invention is markedly excellent in both of the evaluation by the (3R)-1-menthyl 3-hydroxybutyrate alone and evaluation by its joint use with menthol.

Example 4

Comparison Sensory Evaluation (1) Regarding Cooling Effect and Optical Purity

It is already clear from Example 2 that the (3R)-1-menthyl 3-hydroxybutyrate has stronger cooling effect and more excellent refreshing nature than its racemic body. Then, the racemic body 1-menthyl 3-hydroxybutyrate was added to the (3R)-1-menthyl 3-hydroxybutyrate obtained in Example 1 to prepare the (3R)-1-menthyl 3-hydroxybutyrate having the following optical purity, and a 100 ppm aqueous solution was prepared, respectively and sensory evaluation for cooling effect was carried out by ten professional panels having 5 years or more of experience.

As the evaluation method, the 100 ppm aqueous solution was kept in the mouth for 15 seconds and then spat out. Then, regarding the intensity of cooling effect of the racemic body as 3, the score was relatively gotten based on the following five-grade evaluation standard, and the average was calculated to validate the effect. The results are shown in Table 3.

<Evaluation Standard>

5: Very strong
4: Strong
3: Level same as racemic body

2: Weak
1: Very weak

TABLE 3

| | Optical purity of (3R)-1-menthyl 3-hydroxybutylate | | | | | |
|---|---|---|---|---|---|---|
| | 0% e.e. (Racemic body) | 30% e.e. | 50% e.e. | 70% e.e. | 90% e.e. | 98% e.e. |
| Average value of cooling intensity | 3.0 | 3.2 | 3.7 | 4.0 | 4.6 | 4.8 |

(Average value of relative intensity based on 5-grade evalution when regarding racemic body as 3)

It was found from the above results that, based on the racemic body, the optical purity of (3R)-1-menthyl 3-hydroxybutyrate is increased to gradually heighten the cooling intensity. The tendency becomes dominant at 50% e.e. or more, and becomes prominent at 90% e.e. or more.

Example 5

Comparison Sensory Evaluation (2) Regarding Cooling Effect and Optical Purity

The racemic body 1-menthyl 3-hydroxybutyrate was added to the (3R)-1-menthyl 3-hydroxybutyrate obtained in Example 1, and the (3R)-1-menthyl 3-hydroxybutyrate having the following optical purity was prepared, respectively. The obtained (3R)-1-menthyl 3-hydroxybutyrate having each of the optical purity was diluted and dissolved in ethanol/water=40:60 (weight ratio) so as to have a 2 weight % solution to prepare each of test solutions.

500 μL of thus obtained test solution was dropped on a patch pad (37.5mm×50 mm), and the pad was applied on an antebrachial region for 30 minutes. Then, the cooling intensity and persistency of cool-feeling were evaluated.

The evaluation was conducted for each test solutions for 4 times by five professional panels.

When evaluated, the limit was set as follows: left antebrachial region once and right antebrachial region once per day.

Regarding the evaluation of the racemic body as 3, the score was relatively gotten based on the following five-grade evaluation standard, and the average was calculated to validate the effect.

<Evaluation Standard>
5: Very strong
4: Strong
3: Level same as racemic body
2: Weak
1: Very weak

TABLE 4

| | Optical purity of (3R)-1-menthyl 3-hydroxybutylate | | | | | |
|---|---|---|---|---|---|---|
| | 0% e.e. (Racemic body) | 30% e.e. | 50% e.e. | 70% e.e. | 90% e.e. | 98% e.e. |
| Cooing intensity | 3.0 | 3.2 | 3.5 | 3.7 | 4.5 | 4.7 |
| Persistency of cool-feeling | 3.0 | 3.1 | 3.6 | 3.7 | 4.2 | 4.4 |

(Average value of relative intensity based on 5-grade evalution when regarding racemic body as 3)

It was found from the above results that the cooling intensity and persistency are gradually heightened at the optical purity of (3R)-1-menthyl 3-hydroxybutyrate of 50% e.e. or more, and the tendency becomes prominent at 90% e.e. or more.

Example 6

Body Shampoo

A flavor or fragrance composition comprising the sensate composition was obtained from 35 parts by weight of the (3R)-1-menthyl 3-hydroxybutyrate obtained in the above-mentioned Example 1 and 65 parts by weight of a citrus herbal fragrance composition(manufactured by Takasago International Corp.), and a body shampoo was prepared using this in accordance with the following prescription. This product was possessed of a cool-feeling and maintained its cooling effect.

<Body Shampoo Prescription>

TABLE 5

| Components | Blending amount (g) |
|---|---|
| Triethanolamine | 9.00 |
| Lauric acid | 6.00 |
| Myristic acid | 9.00 |
| Polyoxyethylene lauryl sulfosuccinate disodium (1 E.O.) (42%) | 10.00 |
| Alkyl (C8-16) glucoxide | 8.00 |
| Glyceryl laurate | 1.00 |
| 2-Hydroxyethyl distearate | 2.50 |
| Coconut oil fatty acid diethanolamide | 3.00 |
| Propylene glycol | 5.00 |
| Dibutylhydroxytoluene | 0.05 |
| Disodium edetate | 0.10 |
| Ethyl p-oxybenzoate | 0.20 |
| Methyl p-oxybenzoate | 0.10 |
| Flavor or fragrance composition comprising the above sensate composition | 0.95 |
| Purified water | balance |
| Total | 100.00 |

Example 7

Flavor or Fragrance Composition

A flavor or fragrance composition comprising a sensate composition was prepared in the usual way in accordance with the following prescription.

<Flavor or Fragrance Composition Prescription>

TABLE 6

| Components | Blending amount (g) |
|---|---|
| Apple base (mfd. by Takasago International Corp.) | 8.00 |
| Bergamot oil | 14.00 |
| Ethyl acetoacetate | 5.00 |
| Methyl dihydrojasmonate | 23.00 |
| Laurinal | 3.00 |
| Levosandol (mfd. by Takasago International Corp.) | 4.00 |
| Orange oil | 8.00 |
| 10-Oxa-16-hexadecanolide | 8.00 |
| Phenoxanol (mfd. by IFF) | 6.00 |
| Styralyl acetate | 3.00 |
| Thesaron (mfd. by Takasago International Corp.) | 8.00 |
| (3R)-1-menthyl 3-hydroxybutyrate obtained in Example 1 | 20.00 |
| 3-1-Menthoxypropane-1,2-diol | 10.00 |
| Total | 120.00 |

Comparative Example 1

Flavor or Fragrance Composition

A flavor or fragrance composition was prepared in the usual way, by changing the (3R)-1-menthyl 3-hydroxybutyrate in the prescription of flavor or fragrance composition of Example 7 to its racemic body 1-menthyl 3-hydroxybutyrate.

Example 8

Shampoo

In accordance with the following prescription, 100 g of shampoo scented with 1.0 weight % of the flavor or fragrance composition of the above-mentioned Example 7 or Comparative Example 1 was prepared. In comparison with the shampoo scented with the flavor or fragrance composition of Comparative Example 1 (racemic body 1-menthyl 3-hydroxybutyrate was used), the shampoo scented with the flavor or fragrance composition of Example 7 ((3R)-1-menthyl 3-hydroxybutyrate was used) was possessed of a strong cool-feeling and maintained its cooling effect.
<Shampoo Prescription>

TABLE 7

| Components | Blending amount (g) |
| --- | --- |
| Polyoxyethylene lauryl ether sodium sulfate | 14.00 |
| Amidopropylbetaine Laurate | 4.00 |
| Coconut oil fatty acid diethanolamide | 3.00 |
| Cationized cellulose | 0.50 |
| Ethylene glycol distearate | 1.00 |
| Ethyl p-oxybenzoate | 0.25 |
| Citric acid | proper amount |
| Flavor or fragrance composition | 1.00 |
| Purified water | balance |
| Total | 100.00 |

Example 9

Transparent Shampoo

A transparent shampoo was prepared in accordance with the following prescription. This product was possessed of a cool-feeling and maintained its cooling effect.
<Transparent Shampoo Prescription>

TABLE 8

| Components | Blending amount (g) |
| --- | --- |
| Polyquaternium-10 | 10.00 |
| Na lauryl sulfate (30% aqueous solution) | 300.00 |
| Lauroyl sarcosine Na (30% aqueous solution) | 50.00 |
| Cocamidopropyl betaine | 100.00 |
| Coconut oil fatty acid diethanolamide | 40.00 |
| 1,3-Butylene glycol | 20.00 |
| Citric acid | 3.00 |
| Methyl paraben | 2.00 |
| Propyl paraben | 0.50 |
| Disodium edetate | 1.00 |
| 1-Menthol | 6.30 |
| (3R)-1-menthyl 3-hydroxybutyrate obtained in Example 1 | 0.60 |
| Vanillyl butyl ether | 0.10 |
| Citrus type flavor or fragrance | 3.00 |
| Purified water | balance |
| Total | 1000.0 |

The substance of the invention, (3R)-1-menthyl 3-hydroxybutyrate, is a cooling component which has more stronger cooling intensity in comparison with its racemic body and is excellent in the persistency of refresh-feeling and cool-feeling. In addition, according to the invention, there can be provided a sensate composition, which comprises the aforementioned compound having excellent cooling effect and persistency of the cooling effect, and a flavor or fragrance composition, food or drink, fragrance or cosmetic, daily necessities and household goods, oral composition or pharmaceutical, which comprises said sensate composition.

The invention claimed is:

1. A cooling agent comprising (3R)-1-menthyl 3-hydroxybutyrate represented by the formula (I):

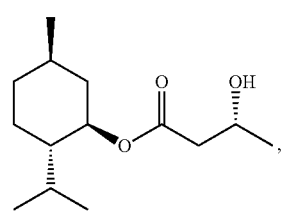

wherein an optical purity at the 3-position hydroxyl group of the (3R)-1-menthyl 3-hydroxybutyrate is 50% e.e. or more.

2. A sensate composition comprising:
(3R)-1-menthyl 3-hydroxybutyrate represented by the formula (I):

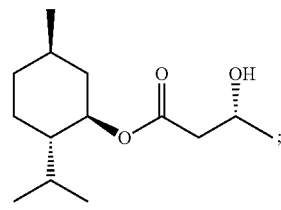

and
at least one component selected from the group consisting of a cooling component other than the (3R)-1-menthyl 3-hydroxybutyrate and a warming component,
wherein an optical purity at the 3-position hydroxyl group of the (3R)-1-menthyl 3-hydroxybutyrate is 50% e.e. or more.

3. The sensate composition according to claim 2, wherein the cooling component other than the (3R)-1-menthyl 3-hydroxybutyrate is at least one component selected from the group consisting of menthol, menthone, camphor, pulegol, isopulegol, cineol, mint oil, peppermint oil, spearmint oil, eucalyptus oil, 3-1-menthoxypropane-1,2-diol, N-alkyl-p-menthane-3-carboxamide, 3-1-menthoxy-2-methylpropane-1,2-diol, p-menthane-3,8-diol, 2-1-menthoxyethanol, 3-1-menthoxypropanol, 1-menthyl lactate, menthone glycerol ketal, menthyl succinate, menthyl glutarate, dimenthyl glutarate and N-methyl-2,2-isopropylmethyl-3-methyl butanamide.

4. The sensate composition according to claim 2, wherein the warming component is at least one component selected from the group consisting of vanillyl ethyl ether, vanillyl propyl ether, vanillin propylene glycol acetal, ethyl vanillin propylene glycol acetal, capsaicin, gingerol, vanillyl butyl ether, 4-(1-menthoxymethyl)-2-phenyl-1,3-dioxolan, 4-(1-menthoxymethyl)-2-(3',4'-dihydroxyphenyl)-1,3-dioxolan, 4-(1-menthoxymethyl)-2-(2'-hydroxy-3'-methoxyphenyl)-1,3-dioxolan, 4-(1-menthoxy-methyl)-2-(4'-methoxyphenyl)-1,3-dioxolan, 4-(1-menthoxymethyl)-2-(3',4'-methylene-dioxyphenyl)-1,3-dioxolan, 4-(1-menthoxymethyl)-2-(3'-methoxy-4'-hydroxyphenyl)-1,3-dioxolan, vanillin acetals, red pepper oil, red pepper oleoresin, ginger oleoresin, nonylic acid vanillylamide, jambu oleoresin, Japanese pepper extract, sanshool-I, sanshool-II, sanshoamide, black pepper extract, chavicine, piperine and spilanthol.

5. A flavor or fragrance composition comprising (3R)-1-menthyl 3-hydroxybutyrate represented by the formula (I) in an amount of 0.001 to 90 weight % based on the total amount of the flavor or fragrance composition:

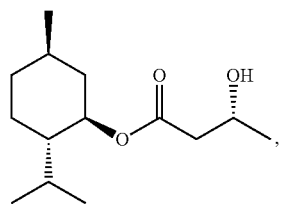

(I)

wherein an optical purity at the 3-position hydroxyl group of the (3R)-1-menthyl 3-hydroxybutyrate is 50% e.e. or more.

6. A product comprising (3R)-1-menthyl 3-hydroxybutyrate represented by the formula (I) in an amount of 0.0001 to 30 weight % based on the total amount of the product:

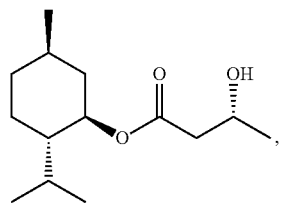

(I)

wherein an optical purity at the 3-position hydroxyl group of the (3R)-1-menthyl 3-hydroxybutyrate is 50% e.e. or more, and wherein the product is selected from the group consisting of a food or drink, a fragrance or cosmetic, a daily necessities and household goods, an oral composition and a pharmaceutical.

7. A flavor or fragrance composition comprising the sensate composition according to claim 2 in an amount of 0.001 to 90 weight % based on the total amount of the flavor or fragrance composition.

8. A flavor or fragrance composition comprising the sensate composition according to claim 3 in an amount of 0.001 to 90 weight % based on the total amount of the flavor or fragrance composition.

9. A flavor or fragrance composition comprising the sensate composition according to claim 5 in an amount of 0.001 to 90 weight % based on the total amount of the flavor or fragrance composition.

10. A product comprising the sensate composition according to claim 2 in an amount of 0.0001 to 30 weight % based on the total amount of the product, wherein the product is selected from the group consisting of a food or drink, a fragrance or cosmetic, a daily necessities and household goods, an oral composition and a pharmaceutical.

11. A product comprising the sensate composition according to claim 3 in an amount of 0.0001 to 30 weight % based on the total amount of the product, wherein the product is selected from the group consisting of a food or drink, a fragrance or cosmetic, a daily necessities and household goods, an oral composition and a pharmaceutical.

12. A product comprising the sensate composition according to claim 4 in an amount of 0.0001 to 30 weight % based on the total amount of the product, wherein the product is selected from the group consisting of a food or drink, a fragrance or cosmetic, a daily necessities and household goods, an oral composition and a pharmaceutical.

13. A method for producing (3R)-1-menthyl 3-hydroxybutyrate represented by the formula (I), wherein an optical purity at the 3-position hydroxyl group of the (3R)-1-menthyl 3-hydroxybutyrate is 50% e.e. or more:

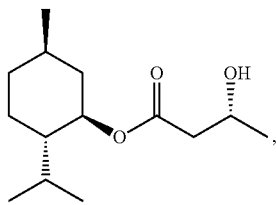

(I)

which comprises subjecting 1-menthyl acetoacetate represented by the formula (II) to asymmetric hydrogenation:

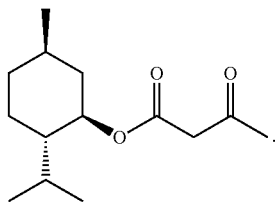

(II)

14. The method for producing (3R)-1-menthyl 3-hydroxybutyrate according to claim 13, which comprises synthesizing the 1-menthyl acetoacetate by subjecting a mixture of 1-menthol and methyl acetoacetate to transesterification in the absence of a catalyst or in the presence of a protonic acid catalyst, and in the absence of a solvent or in an aliphatic hydrocarbon having 5 to 8 carbon atoms.

15. A method for imparting a cooling sensation to a flavor or fragrance composition, a food or drink, a fragrance or cosmetic, a daily necessities and household goods, an oral composition or a pharmaceutical, which comprises adding (3R)-1-menthyl 3-hydroxybutyrate represented by the formula (I) to the flavor or fragrance composition, food or drink, fragrance or cosmetic, daily necessities and household goods, oral composition or pharmaceutical:

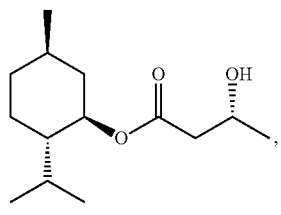
(I)
wherein an optical purity at the 3-position hydroxyl group of the (3R)-1-menthyl 3-hydroxybutyrate is 50% e.e. or more.
16. (3R)-1-menthyl 3-hydroxybutyrate represented by the formula (I) having an optical purity of 50% e.e. or more at the 3-position hydroxyl group:
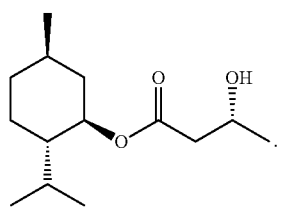
(I)
* * * * *